United States Patent [19]

Caston et al.

[11] 3,981,983

[45] Sept. 21, 1976

[54] RAPID, RADIOCHEMICAL-LIGAND BINDING ASSAY FOR METHOTREXATE

[75] Inventors: J. Douglas Caston, Cleveland Heights, Ohio; Barton A. Kamen, Rockville Centre, N.Y.

[73] Assignee: Case Western Reserve University, Cleveland, Ohio

[22] Filed: June 30, 1975

[21] Appl. No.: 591,310

[52] U.S. Cl. .............................. 424/1.5; 23/230 B; 195/103.7
[51] Int. Cl.² ................. G01N 33/00; G21H 5/02; A61K 43/00
[58] Field of Search ............... 424/1, 115; 23/230 B; 195/103.7

[56] References Cited
OTHER PUBLICATIONS

Raso et al., Cancer Research, vol. 35, No. 6, 1975, pp. 1407–1410.
Bohuon et al., Clinical Chemica Acta, vol. 57, No. 3, 1974, pp. 263–267.
Levine et al., Res. Commun. Chem. Pathol. Pharmacol., vol. 9, No. 3, 1974, pp. 543–554.
Freedman et al., Journal of Clinical Pathology, vol. 26, No. 4, 1973, pp. 261–267.

*Primary Examiner*—Benjamin R. Padgett
*Assistant Examiner*—Christine M. Nucker
*Attorney, Agent, or Firm*—McNenny, Pearne, Gordon, Gail, Dickinson & Schiller

[57] ABSTRACT

A radiochemical ligand binding assay for methotrexate is provided. A binder factor comprising a partially purified dihydrofolic acid reductase preparation is employed. The binder factor is conveniently prepared by homogenizing a factor containing animal organ such as liver, and extracting with isotonic saline and ammonium sulfate. A binder cofactor, $NADPH_2$, is also employed in the binding reaction. The procedure contemplates both direct and sequential assay techniques, and it is not interfered with by vast excesses of many natural folate derivatives.

12 Claims, 6 Drawing Figures

RAPID, RADIOCHEMICAL-LIGAND BINDING ASSAY FOR METHOTREXATE

BACKGROUND OF THE INVENTION

The folic acid analogue amethopterin, N-[p-(2,4-diamino-6-pteridylmethyl)methylaminobenzoyl]-glutamic acid, has been used for about 25 years as an anti-neoplastic agent. The related compounds aminopterin, N-{p-[(2,4-diamino-6-pteridylmethyl)amino] benzoyl}-glutamic acid, and dichloro-methotrexate, N-[p-(2,4-diamino-3,5-dichloro-6-pteridylmethyl)methylaminobenzoyl]-glutamic acid, are similarly employed. These compounds are highly toxic, and the concentration of the same in a particular patient's system can vary despite controlled dosages. Accordingly, it is essential that the concentration in the recipient's system of the particular compound being administered be known and readily determinable at all times during treatment. The present invention provides a simple, economical and rapid method for determining the concentration of methotrexate or its assay equivalents in biological material, especially serum and cerebrospinal fluid.

As indicated above, amethopterin (hereinafter referred to as methotrexate or MTX) is widely used, and the mechanism by which it acts in biological systems has been studied rather extensively as noted in Bertino, J. R., "The Mechanism Of Action Of The Folate Antagonists In Man," Cancer Research 23, pages 1286 - 1306, 1963. These prior art studies and related efforts have disclosed the binding of methotrexate by dihydrofolic acid reductase (hereafter referred to as folic acid reductase), and assay techniques wherein determinations of enzymatically reactive substances are made by monitoring changes in the reaction solution which are proportional to the reaction or amount of the enzyme to be determined. However, it is believed that no direct binding studies using radiolabeled methotrexate or the further compounds noted above have been done with folic acid reductase.

The binding reaction techniques of the present invention are to be distinguished from prior art enzyme determinations wherein the enzyme is not bound per se, but rather ascertained by indirect means such as competitive oxidation of a coreactant. The subject binding techniques are also distinguished from proteinantibody radioimmunoassay techniques which are directed to determinations of complex, high molecular weight protein molecules for which specific antibodies are typically obtained by animal immunizing procedures. In contrast, the subject techniques employ an enzyme binder preparation which forms a stable complex with the ligand to be determined in the presence of a cofactor. The use of an enzyme binder preparation is advantageous since it generally has a higher specificity, a higher affinity and it is more readily available as compared with antibody materials. Thus, the procedures of the present invention employ radiochemical ligand binding techniques to provide a rapid and sensitive assay.

SUMMARY OF THE INVENTION

In accordance with the present invention, a radiochemical assay for determining the concentration of methotrexate or its assay equivalents in biological material is provided. Bound amounts of the labeled compound and known concentrations of the unlabeled compound to be determined are radioisotopically related in a first system containing a predetermined amount of the labeled compound, a binder factor for the compound, a binder cofactor and a predetermined amount of the unlabeled compound. In a second system which is identical with the first system but for the substitution of the test sample of the biological material to be determined for the unlabeled compound, the bound amount of the labeled compound is radioisotopically determined. The concentration of the compound in the test sample is then determined by correlating the bound amount of the labeled compound determined in the second system through the relationship determined in the first system. The radioisotopic relationships and determinations can be made in both direct and sequential assay techniques.

The binder factor comprises a partially purified folic acid reductase prepared by homogenizing and extracting appropriate biological materials containing the binder factor. The binder factor is identified as such and as folic acid reductase by its ability to reduce labeled folic acid to tetrahydrofolic acid, and by its ability to bind $^3$H-MTX. The binder factor is available from a wide range of natural sources since it is present in substantially all "free living materials." Mammalian liver has been found to provide a high binder factor per weight ratio and a convenient system for extraction of the factor or enzyme. The extraction technique employed in the case of guinea pig livers is described in detail below. Examples of other liver sources include hogs and humans. In further illustration of the range of binder factor sources, it is noted that the binder factor may be extracted with variation in technique from human white cells and bacteria.

It has been found necessary to employ reduced nicotinamide adenine dinucleotide phosphate (NADPH$_2$) as a binder cofactor which participates in the bound complex and assures stability of the same. Further, it has been found that the folic acid reductase or binder factor has a high specificity for the particular cofactor necessary for formation of a stable complex.

MATERIALS AND METHODS

Figure 1A:
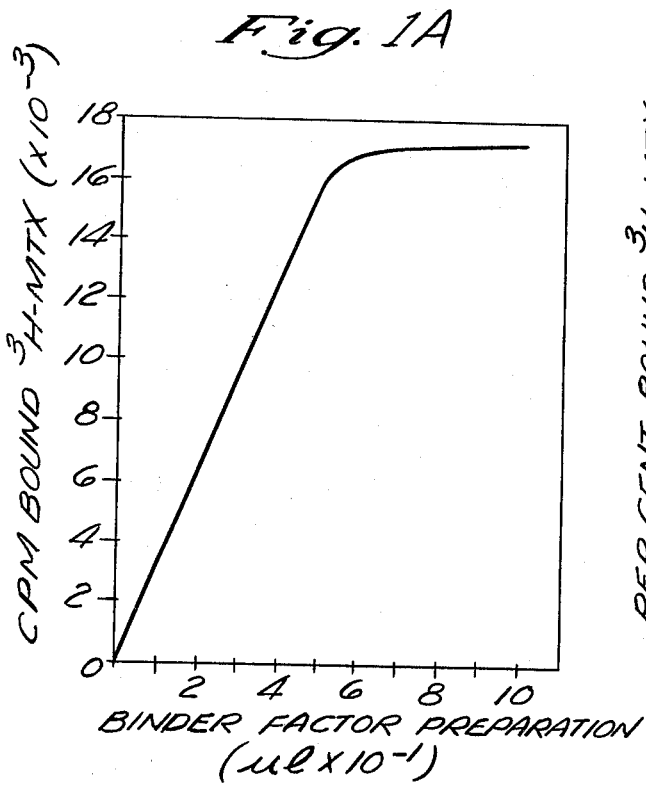
FIG. 1A demonstrates the binding of labeled methotrexate as a function of increasing binder concentration in accordance with sequential assay techniques.

The assay reaction is carried out in an aqueous solution of 0.01 M potassium phosphate, 0.15 M potassium chloride, pH 6.0, hereinafter referred to as buffer A. In the assay procedure, buffer A has added thereto about 1 mg of albumin per ml and other additons as noted.

The stock albumin solution was prepared by dissolving 10 mg of bovine albumin (Calbiochem Co.)/ml of distilled water and then adding 7 mg of powdered activated charcoal (Norit A, Matheson Colman and Bell) per ml of solution. The suspension was stirred slowly for 20 minutes at 4°C, and then was centrifuged for 20 minutes at 12,000 × G to pellet the charcoal. The clear supernatant fluid was frozen in small aliquots at −30°C until needed.

As previously indicated, a binder cofactor comprising reduced nicotinamide adenine dinucleotide phosphate or $NADPH_2$ was added to the reaction solution in the amounts noted below at the time of the assay. $NADPH_2$ in buffer A with albumin was stable for several days at 4°C, but it was usually added fresh at the time of assay.

Tritiated methotrexate ($^3$H-MTX, Amersham Semale) with a specific activity of 10 to 20 Ci per mmole (millimole) is conveniently used as a tracer or labeled compound. In this regard, $^3$H-MTX is also used as the labeled compound in determinations of aminopterin and dichloro-methotrexate. The $^3$H-MTX was dissolved in 0.05 M tris(hydroxymethyl)aminomethane hydrochloride buffer, pH 7.5 to a final concentration of 100 to 200 pmoles/ml (picomoles/ ml) and frozen at −80°C in small aliquots until needed. Depending upon the level of sensitivity needed for a given assay, the $^3$H-MTX stock was diluted in buffer A to a concentration of 5 to 20 pmoles/ml. Unlabeled methotrexate (Lederle Co.) in a standardized solution of 25 mg/ml was diluted in a ratio of 1 to 10,000 in distilled water, and then further diluted in buffer A to the desired concentration for assay. When necessary, MTX and $^3$H-MTX were purified by the method of Johns et al, "The Metabolism of Tritiated Folic Acid in Man," *J. Clin. Invest*, 40, pages 1684 – 1695, 1961.

Charcoal coated with Dextran T-10 (dextran, a polysaccharide, having a molecular weight of about 10,000, Pharmacia) was prepared by mixing equal volumes of a 5% suspension of Norit A and a 1% solution of Dextran T-10, both in distilled water. Excess Dextran T-10 was removed by collecting the coated charcoal on a coarse sintered glass filter, washing with one volume of distilled water and finally resuspending the coated charcoal in the original volume of distilled water. The resultant mixture was stored at 4°C and was stable for 3 to 4 weeks. It was stirred vigorously immediately prior to each use. The dextran provides a "sieve function" relative to the bound and unbound MTX, and other materials of suitable molecular weight may be employed.

The binder factor or folic acid reductase was prepared from guinea pig liver according to the method of Bertino et al, "Dihydrofolate Reductase From Guinea Pig Liver And Small Intestine," *Biochemical Pharmacology* 15, pages 563 - 571, 1966 modified as noted below. The livers from freshly killed guinea pigs were rinsed in cold isotonic saline, suspended in 3 volumes (weight/volume) of the same, and homogenized in an Omnimixer (Sorvall, Inc.) for two minutes at 90 volts. The pH of the homogenate was adjusted to 5.1 with 1.0 N HCl. The homogenate was centrifuged at 12,000 × G for 15 minutes, and the pellet was discarded.

Ammonium sulfate was added to the supernatant to 55% of saturation at 4°C and, when necessary, the pH was adjusted to 6.0 with 1.0 N KOH. After standing for 30 minutes at 4°C, the precipitate was collected by centrifugation for 15 minutes at 12,000 × G and discarded. The supernatant was brought to a final ammonium sulfate concentration of 70% of saturation, again keeping the pH at 6.0, and stored overnight at 4°C. The resultant precipitate was recovered by centrifugation, as above, and dissolved in a minimal volume of 0.01 M potassium phosphate buffer, pH 7.0, which was 0.01 M with respect to KCl. The burgundy colored solution was applied to a Sephadex G-50 column (5 × 100 cm) equilibrated in 0.01 M potassium phosphate, pH 7.0, and 0.2 M KCl; the same buffer was used for elution of the sample.

The eluted material from the column was collected in 5 ml samples, and the binder factor or folic acid reductase eluted from the column behind the excluded volume which was marked by the hemoglobin peak. Sephadex permitted a rapid removal of ammonium sulfate and also gave a partial purification of the binder. Yields of 60% to 80% of the activity present in the crude homogenate were obtained with this methodology.

The binder factor was identified by its ability to reduce labeled folic acid to tetrahydrofolic acid, Rothenberg, S. P., "A Rapid Radioassay For Folic Acid Reductase And Amethopterin," *Anal. Biochem*, 16, pages 176 – 179, 1966. It was also identified by its ability to bind $^3$H-MTX. The MTX binding capacity of the pooled peak fractions was determined by titration of a standard MTX concentration against increasing amounts of binder factor or by titration of a given amount of binder factor against increasing concentrations of MTX, as described below.

The binder factor preparation was stored in small aliquots at -80°C until needed. Because folate reductase becomes activated upon freeze-thawing, the binding capacity was checked after each thawing, if the aliquot was used more than one time. Although crude homogenate or the 55-70% ammonium sulfate fraction after dialysis was suitable for use in the assay, the simple procedure described herein produced a stable and reproducible MTX binding preparation. Four to five livers appropriately processed yielded enough binder for several thousand assays.

The samples were counted using standard liquid scintillation techniques well known in the art in a scintillation fluid which, for example, may be prepared by mixing equal volumes of toluene containing 13.7 grams of 2,5-diphenyloxazole (PPO/1, scintillation grade) and 0.28 grams of 1,4-bis-2-(4-methyl-5-phenyloxazolyl) benzine (POPOP/1, scintillation grade), and a nonionic wetting agent, such as an alkylene oxide condensation product with an alkyl phenol, e.g. nonyl phenol plus 9 mols ethylene oxide (Triton X-100, Research Products International). Counting efficiency was about 30%, and the samples were counted to a 2.5% or less statistical error.

PREPARATION OF STANDARDS AND ASSAY PROCEDURE

The subject assay procedure is similar in technique to other radioligand binding assays or radioimmunoassays. The procedure is based upon the discovery that the binder factor preparation or folic acid reductase in the presence of $NADPH_2$ forms a stable complex with labeled and unlabeled MTX, and that MTX bound to the binder factor is not adsorbed to charcoal coated with dextran whereas unbound or free MTX is readily adsorbed and can be removed from solution by removing the charcoal coated with dextran. The bound complex is aptly characterized as an enzyme-ligand-ligand complex comprising the binder factor preparation, the bound MTX and the NADPH$_2$ binder cofactor.

As previously indicated, the subject assay procedure enable the MTX concentration of any sample to be determined by either direct competitive binding or sequential binding methodology. Each methodology offers special advantages, depending upon the required level of sensitivity and other requisites of a given sample. In view of the relatively low specific actvity of commercially available $^3$H-MTX, the sequential procedure has been used more frequently since it is the more sensitive of the two techniques, and it will be described in greater detail herein. Further, it is convenient in some instances to either increase the range of the standards or to greatly dilute the sample to be assayed since the samples contain widely varying amounts of MTX. In either instance, the general methodology is not altered and the stoichiometry of the binding reaction is not changed.

Figure 1B:
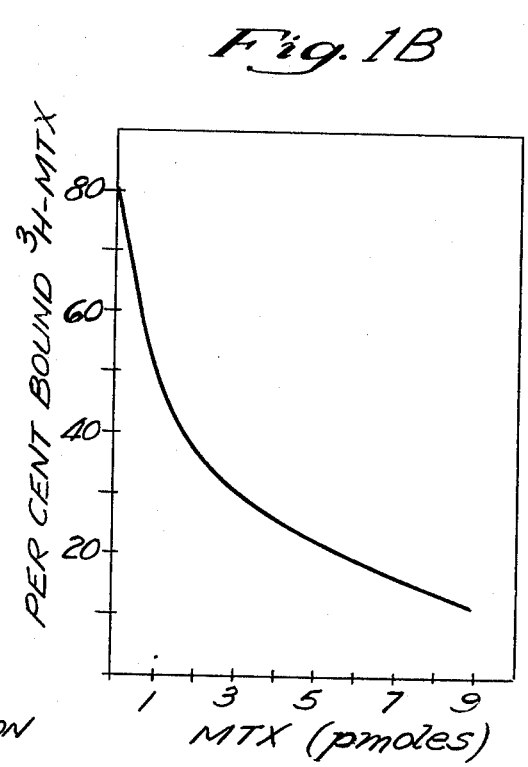
FIG. 1B is a characteristic isotope dilution curve obtained in accordance with direct competitive assay techniques.

Referring to FIGS. 1A to 1B, the determination of the binding capacity of the binder is illustrated in sequential and direct techniques. In FIG. 1A, $^3$H-MTX binding is shown as a function of increasing binder concentration. Increasing amounts of binder preparation were incubated in 1.1 ml of buffer A with albumin containing 0.1 $\mu$mole (micromole) NADPH$_2$ and 3.5 pmoles $^3$H-MTX for 15 minutes at 4°C. The reaction was terminated and the samples were counted as described in greater detail below. In FIG. 1B, a characteristic isotope dilution curve was obtained by incubating unlabeled MTX in the amounts indicated with 1.5 pmoles of $^3$H-MTX and enough binder to bind about 1.2 pmole of MTX. This curve is described in greater detail below.

After first determining the binding capacity of the binder preparation for MTX, the standard curves can be determined for sequential and direct assay techniques. The sequential standard curve is shown in FIG. 2A, and the direct competitive curve is shown in FIG. 2B.

Figure 2A:
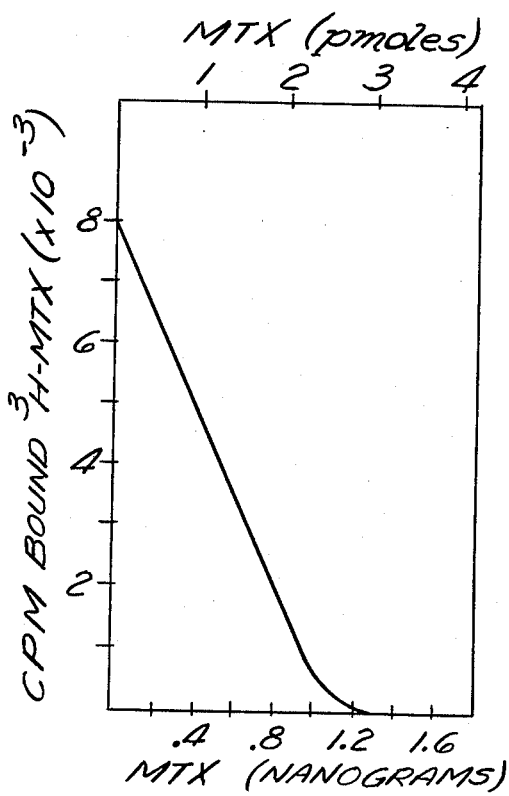
FIG. 2A is a typical standard curve for the determination of methotrexate concentration with sequential assay techniques.
Figure 2B:
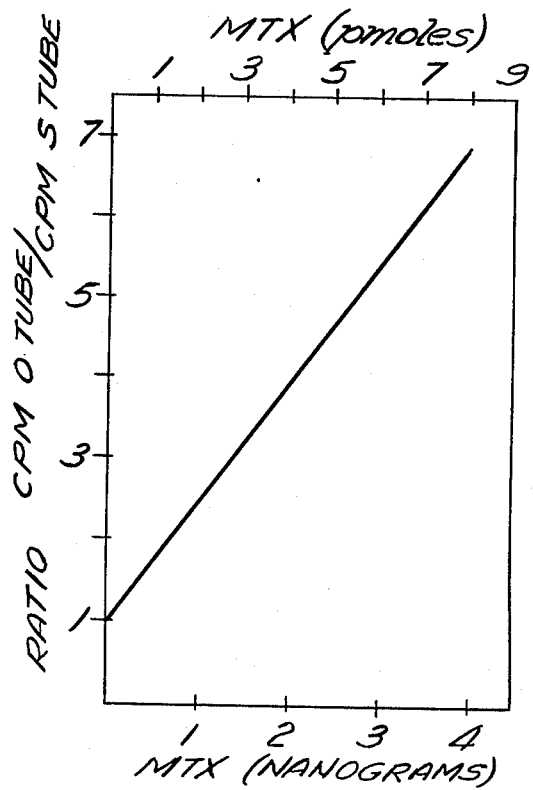
FIG. 2B is a typical standard curve for determination of methotrexate concentration with direct competitive assay techniques.

Referring to FIG. 2A, a constant amount of the binder having a binding capacity of 1 nanogram was incubated in sample tubes with increasing amounts of unlabeled MTX for about 10 minutes at 4°C in the dark in a first incubation period. The amount of unlabeled MTX was progressively increased to about 1.5 times the predetermined binding capacity of the binder in order to assure saturation. This left progressively fewer binding sites for the $^3$H-MTX which was subsequently added. Because of the greater sensitivity achieved by the sequential method of addition, the MTX stock solution was diluted arithmetically at 50 to 100 picogram intervals, rather than geometrically as is more common in competitive binding assays.

At the end of the first incubation period, $^3$H-MTX was added and the incubation was continued for an additional 10 minutes. To obtain consistent results, the amount of $^3$H-MTX added exceeded the binding capacity of the binder preparation by 30 to 50%. The reaction was terminated by the addition of ice cold charcoal coated with dextran which adsorbs unbound $^3$H-MTX and MTX. After centrifugation for 10 minutes at 2,000 – 3,000 × G to pellet the charcoal, the radioactivity in the clear supernatant was determined by liquid scintillation counting. The supernatant of each sample tube was poured into a counting vial which contained 10 ml of scintillation fluid.

As quality checks on the binder and $^3$H-MTX, a charcoal control (C) comprising a sample tube without binder, and a maximum binding control (mbc) comprising a sample tube containing twice the standard amount of binder were included in each assay. In addition, a zero tube comprising a sample tube with the standard amount of binder was also prepared. These controls checked the purity of the $^3$H-MTX and determined if the amount of binder was appropriate for the assay. Ideally, if the charcoal adsorbed all free MTX and the $^3$H-MTX were 100% pure then the charcoal control would be background. In practice, this control was 0.5 – 1.5% of the total counts per minute (cpm) incubated. By similar reasoning, assuming the binding of $^3$H-MTX is essentially irreversible, and proceeds to completion, the maximum binding control will be equal to the total cpm incubated (standard). In practice, the maximum binding control was 75 to 80% of the total cpm incubated, and the zero tube about 80% of the maximum binding control. When the purity of the $^3$H-MTX fell below 60 to 65% as judged by comparing the maximum binding control to the standard, the $^3$H-MTX was repurified (Johns et al, "The Metabolism Of Tritiated Folic Acid In Man," supra).

To construct the standard curve obtained with the sequential assay procedure, it is necessary only to subtract the cpm in the charcoal control from the cpm in the standards to yield the net cpm bound which is then plotted against the concentration of the MTX standards as shown in FIG. 2A. The procedure employed in providing the standard curve of FIG. 2A is detailed in Table I.

TABLE I

| | | | Protocol for Sequential Ligand Binding Procedure | | | |
|---|---|---|---|---|---|---|
| Sample description | (1) Buffer | (2) MTX stds. | (3) Sample | (4) MTX Binder | (5) $^3$H-MTX | (6) CCD |
| C | 0.75 ml | — | — | — | 0.1 ml | 1.0 ml |
| mbc | | — | — | 0.2 ml | | |
| Zero Tube | | — | — | 0.1 ml | | |
| MTX Stds. (nanogms. of MTX) | | | | | | |
| 0.05 | | 0.1 ml | — | 0.1 ml | | |
| 0.1 | | | — | Incubate | Incubate | Spin at |
| 0.3 | | | — | 10 minutes | 10 minutes | 2000 –3000 × G |
| 0.5 | | | — | at 4°C | at 4°C | and count |
| 0.7 | | | — | | | as described |
| 0.9 | | | — | | | |
| 1.1 | | | — | | | |
| 1.3 | | | — | | | |
| 1.5 | | | — | | | |
| Sample | | — | 0.1 | | | |

TABLE I-continued (1) Buffer A containing 1 mg albumin per ml and 0.1 μmole NADPH₂ per sample.
(2) MTX standard. The stock MTX is diluted as previously described and then further diluted in buffer A to appropriate concentrations. In this case, 0.5 to 15 nanograms/ml.
(3) Samples are diluted in buffer A so that 0.1 to 100 μl of sample is assayed.
(4) Binder has 1.0 nanogram MTX binding capacity per 0.1 ml solution.
(5) 0.1 ml solution contains 1.3 - 1.5 nanograms ³H-MTX.
(6) CCD = charcoal coated with dextran. This adsorbs free MTX instantaneously. Tubes can be centrifuged as soon as the CCD is added.

As indicated above, the assay may also be performed in accordance with direct competitive assay procedures. In this instance, the reaction was carried out at 4°C in a total volume of 1.2 ml. To 0.9 ml of buffer A containing about 1 mg of albumin and 0.1 μmole NADPH₂/ml, were added 0.1 ml standard MTX solution containing 5 to 90 pmoles/ml and 0.1 ml ³H-MTX solution containing about 1.5 pmoles ³H-MTX. The reactants were mixed and the incubation was started by the addition of 0.1 ml binder preparation having a binding capacity of 1 to 1.2 pmoles MTX which is enough to bind 70 to 80% of the ³H-MTX. After shaking gently to assure mixing, the reaction was incubated for 10 minutes. The incubation was terminated by addition of charcoal coated with dextran, and the samples were further processed in the same manner as in the sequential assay technique.

The standard curve obtained with the direct competitive assay is shown in FIG. 2B in accordance with the method of Burger et al., "A Generalized Computer Program For The Treatment Of Data From Competitive Binding Assays Including Radioimmunoassays," J. Lab. Clin. Med., 80, pages 164 - 174, 1974. The curve shown in FIG. 2B was obtained by calculating the ratio of the net cpm in the zero tube (the standard containing no unlabeled MTX solution) to the net cpm in the standard tubes, and then plotting these ratio values as a function of the amount of unlabeled MTX. This produces a straight line that crosses the ordinate at a ratio of 1.0 and reaches a ratio of 2.0 when the concentration of the unlabeled MTX equals the concentration of ³H-MTX. Alternatively, the direct competitive assay curve may be plotted as shown in FIG. 1B. In this instance, the net cpm in any sample is calculated by subtracting the charcoal control value from the total number of cpm in the sample. The percent ³H-MTX bound in a given sample is calculated in accordance with the following formula:

$$\% \,^3\text{H-MTX bound} = \frac{\text{cpm sample-C}}{\text{cpm mbc-C}} \times 100$$

To determine the amount of MTX in any sample it is only necessary to obtain the net cpm bound (or the ratio) and compare this value to the known standards. For example, to measure the amount of MTX in a serum sample or cerebrospinal fluid (CSF) sample by either method, an appropriate amount of the sample contained in 0.1 ml solution is substituted for the MTX standard, assayed and correlated with an appropriate standard curve.

Generally, it has been found that the MTX concentration of serum or CSF samples of individuals receiving chemotherapy for psoriasis or acute lymphocytic leukemia varied widely based upon the time of sampling relative to drug administration, so that several concentrations of the sample were assayed. Empirically, it has been found that 0.1, 0.5, 1.0, 5, 10, 50 and 100 μl (microliters) of undiluted sample produced at least 2 or 3 points within the concentration range of the routine standard curve, so that a reliable value could be calculated.

The reliability of the methodology was ascertained by assaying samples of serum and cerebrospinal fluid (CSF) from patients who had received MTX, and from serum and CSF samples to which MTX was added at several concentrations. MTX was also added to samples containing "endogenous" MTX, and additional recovery studies were performed on these samples. The samples were obtained from patients at intervals varying from 6 hours to 6 days after the oral, parenteral or intrathecal administration of MTX. The exogenous MTX was added at the time of the assay. The samples were assayed both before and after heat denaturation to destroy possible endogenous MTX binders. The results of these studies are summarized in Table II.

TABLE II

| | Determination of Serum Cerebrospinal MTX | | | | |
|---|---|---|---|---|---|
| Sample | Endogenous MTX | Exogenous MTX | Expected | Actual | % Recovery[1] |
| | ←――――――― Nanograms per ml ―――――――→ | | | | |
| Serum | | | | | |
| A | — | 1 | 1 | 0.96 | 96 |
| B | — | 5 | 5 | 5.1 | 100.2 |
| C | — | 50 | 50 | 47 | 94 |
| D | 17 | 5 | 22 | 23 | 105 |
| E | 130 | 50 | 180 | 176 | 98 |
| F | 140 | 10 | 150 | 152 | 101 |
| CSF | | | | | |
| A | — | 1 | 1 | 1 | 100 |
| B | — | 5 | 5 | 4.8 | 96 |
| C | — | 50 | 50 | 52 | 104 |
| D | 8 | 1 | 9 | 8.7 | 97 |
| E | 8 | 10 | 18 | 15.9 | 88 |
| F | 8 | 50 | 58 | 60 | 103 |

[1]% Recovery = $\frac{\text{assayed value}}{\text{expected value}} \times 100$

The samples in Table II were assayed by sequential binding procedures in accordance with the present invention, and they were assayed at multiple dilutions as previously described. The points falling between 0 and 0.8 nanograms on the standard curve of FIG. 2A were used to calculate the MTX concentration. The mean standard deviation for any sample was ±5%, and the % recovery ranged from 88% to 105% of the actual MTX concentration as reported in Table II. There was no difference between boiled and unboiled samples, and none of the test samples bound $^3$H-MTX. Further, the presence of ascorbic acid did not affect the assay.

The specificity of the binder was determined by incubating the following compounds in direct competitive and sequential binding assays with $^3$H-MTX: pteroylmonoglutamate (Folic Acid, Nutritional Biochemicals); 5-methyltetrahydrofolic acid (Sigma Chemical Co.); 5-formyltetrahydrofolic acid (Leucovorin, Lederle Co.); adenosine, guanylic acid, para-aminobenzoylglutamate and 6-carboxypterin (Sigma Chemical Co.); pteroylheptaglutamate and aminopterin.

Figure 3:
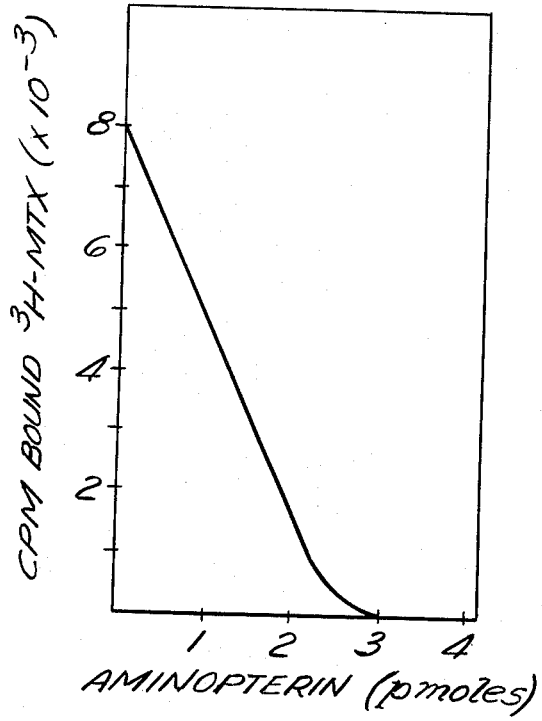
FIG. 3 is a typical standard curve for the determination of aminopterin concentration with sequential assay techniques.

Of all the compounds tested, only MTX and aminopterin competed for $^3$H-MTX binding sites. A typical standard curve obtained for aminopterin is shown in FIG. 3, the methodology employed in its preparation being the same as that used in the preparation of FIG. 2A. The other folate derivatives did not compete even when present in a 200 fold excess relative to the $^3$H-MTX concentration. Further, at the concentration of reactants used in the standard curves, the binder preparation did not bind $^3$H-folic acid or $^{14}$C-5-methyltetrahydrofolic acid.

In addition to determining the binding specificity of the preparation, other experiments studying the kinetics of $^3$H-MTX binding were done. Enzymatic activity of folic acid reductase from many sources demonstrates two pH optima, at about 5 and 7.5. The binding of $^3$H-MTX was also found to be pH dependent but had a single broad optimum between pH 6 and 7.

Figure 4:
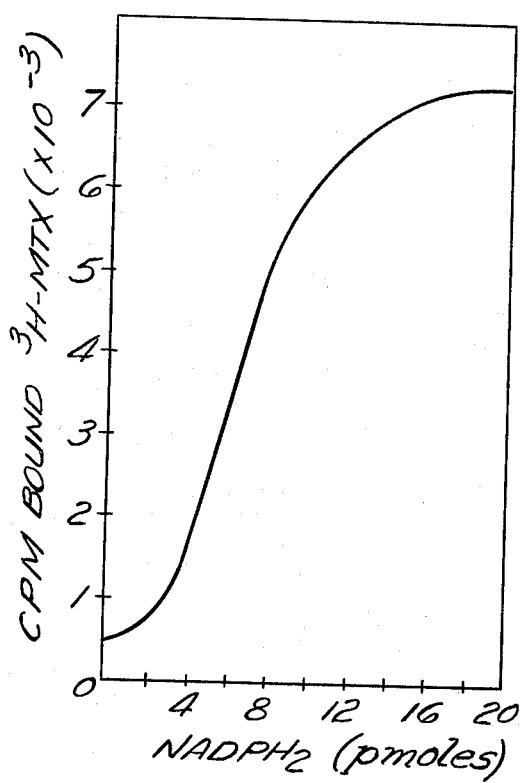
FIG. 4 demonstrates the dependency of methotrexate binding on NADPH$_2$.

Binding of MTX was found to be dependent on the presence of NADPH$_2$, as shown in FIG. 4. In this instance, a constant amount of binder factor having a binding capacity of 3.0 pmole of MTX was incubated with 3.5 pmole of $^3$H-MTX and increasing amounts of NADPH$_2$ in a final volume of 1.1 ml. The maximum binding was identical to the binding observed in the presence of 0.1 μmole NADPH$_2$. Even in this relatively impure preparation of folate reductase, the amount of NADPH$_2$ necessary for maximum binding of $^3$H-MTX is small, the molar ratio of NADPH$_2$:MTX being 3 - 4:1.

Nicotinamide adenine dinucleotide phosphate (NADP, Sigma Chemical Co.) or nicotinamide adenine dinucleotide (NAD, Sigma Chemical Co.) at 1,000 times optimal the concentration of NADPH$_2$ did not allow binding of $^3$H-MTX. Also, when NADPH$_2$ was present only in slight excess to that amount needed for maximal binding of MTX, the latter two compounds did not inhibit the binding reaction until their concentration reached several thousand fold excess to that of NADPH$_2$.

Although the binder factor can use NADH to reduce folic acid or dihydrofolic acid to tetrahydrofolic acid (Bertino et al, "Dihydrofolate Reductase From Guinea Pig Liver And Small Intestine," supra), only 40% of maximum binding of MTX was obtained when this cofactor was substituted for NADPH$_2$, even at concentrations up to 200,000 times the optimal amount of NADPH$_2$. Thus, the binder has a great specificity not only for MTX and aminopterin but also for the cofactor necessary for stable complex formation.

The rate of complex formation was very fast. At an initial concentration of $10^{-9}$M MTX and an equal number of binding sites, the rate was 10% per second at 4°C or $10^{-13}$ moles of MTX binder complex formed per sec. This rate was constant until 85 - 90% of maximal binding was achieved. The complex was stable in the presence of 100 fold excess of NADPH$_2$ for at least 60 hours at 4°C. Accordingly, the incubation periods in either sequential or direct techniques may be as short as two minutes and as long as 24 hours without adversely affecting the assay procedures.

The identification of the binder factor as folic acid reductase is inferred from the observation that when the MTX binding capacity of a given preparation was just saturated with MTX, there was no demonstrable folic acid reductase activity. Further, when the 55 to 70% ammonium sulfate preparation of liver was chromatographed on Sephadex G-50, folic acid reductase and MTX binding co-chromatographed.

In accordance with the methods of the present invention, a partially purified preparation of folic acid reductase enables both direct competitive and sequential radioligand binding assays for methodtrexate. The methods can be applied to biological materials and can measure as little as $5 \times 10^{-14}$ mole of methotrexate with acceptable reliablity. In the foregoing procedures, we may use aminopterin and dichloro-methotrexate in place of methotrexate.

What is claimed is:

1. A method for determining the concentration of methotrexate in biological material comprising the steps of:
   a radioisotopically relating the bound amounts of labeled methotrexate and known concentrations of methotrexate in a first system containing a predetermined amount of labeled methotrexate, a binder factor for methotrexate, a binder cofactor, and a predetermined amount of unlabeled methotrexate;
   b radioisotopically determining the bound amount of said labeled methotrexate in a second system containing said predetermined amount of labeled methotrexate, said binder and said binder cofactor, and a test sample or said biological material to be determined; and
   c correlating the bound amount of labeled methotrexate determined in step (b) through the relationship determined in step (a) to ascertain the concentration of methotrexate in the test sample.

2. A method in accordance with claim 1 wherein said binder factor and said unlabeled methotrexate are blended together before the addition of said labeled methotrexate to said first system, and said binder factor and said test sample are blended together before the addition of said labeled methotrexate to said second system.

3. A method in accordance with claim 2 wherein said first and second systems are incubated for at least 2 minutes prior to the addition of said labeled member.

4. A method as set forth in claim 1 wherein said unlabeled methotrexate and said labeled methotrexate in step (a), and said test sample and said labeled methotrexate in step (b) are blended together prior to the addition of said binder factor in each of said steps.

5. A method as set forth in claim 1 wherein said binder factor is a partially purified preparation of folic acid reductase.

6. A method as set forth in claim 1 wherein said binder factor is mammalian liver folic acid reductase.

7. A method as set forth in claim 1 wherein said binder factor is guinea pig liver folic acid reductase.

8. A method as set forth in claim 1 wherein said binder cofactor is reduced nicotinamide adenine dinucleotide phosphate.

9. A method as set forth in claim 1 wherein said first and second systems include a buffer comprising an aqueous solution of potassium phosphate and potassium chloride.

10. A method as set forth in claim 1 wherein said biological material is serum.

11. A method as set forth in claim 1 wherein said biological material is cerebrospinal fluid.

12. A method for determining the concentration of aminopterin in biological material comprising the steps of:
   a. radioisotopically relating the bound amounts of labeled methotrexate and known concentrations of aminopterin in a first system containing a predetermined amount of labeled methotrexate, a binder factor for methotrexate and aminopterin, a binder cofactor, and a predetermined amount of unlabeled aminopterin;
   b radioisotopically determining the bound amount of said labeled methotrexate in a second system containing said predetermined amount of labeled methotrexate, said binder and said binder cofactor, and a test sample of said biological material to be determined; and
   c correlating the bound amount of labeled methotrexate determined in step (b) through the relationship determined in step (a) to ascertain the concentration of aminopterin in the test sample.

* * * * *